United States Patent [19]

Lee

[11] 4,260,392

[45] Apr. 7, 1981

[54] METHOD AND APPARATUS FOR OBTAINING AN ALIQUOT OF A LIQUID IN A GEL MEDIUM

[75] Inventor: Martin J. Lee, Leonia, N.J.

[73] Assignee: Technicon Instruments Corporation, Tarrytown, N.Y.

[21] Appl. No.: 922,611

[22] Filed: Jul. 7, 1978

[51] Int. Cl.³ .................. G01N 33/00; G01N 33/48; C12Q 1/00

[52] U.S. Cl. .................. 23/230 R; 23/230 B; 422/56; 422/58; 422/66; 435/4; 435/25; 435/26; 435/299; 435/301; 435/805

[58] Field of Search .................. 23/230 R, 230 B; 422/56, 58, 66, 69; 195/103.5 R; 435/299–301, 805, 4, 25, 26

[56] References Cited

U.S. PATENT DOCUMENTS

| | | | |
|---|---|---|---|
| 3,146,163 | 8/1964 | Brewer | 195/103.5 R |
| 3,368,872 | 2/1968 | Natelson | 422/66 |
| 3,526,480 | 9/1970 | Findl et al. | 422/66 |
| 3,585,004 | 6/1971 | Mast | 422/56 |
| 3,607,093 | 9/1971 | Stone | 435/299 X |
| 3,725,004 | 4/1973 | Johnson et al. | 23/230 B |
| 3,791,930 | 2/1974 | Saxholm | 195/103.5 R |
| 3,798,004 | 3/1974 | Zerachia et al. | 422/56 |
| 3,814,670 | 6/1974 | Freake et al. | 435/301 |
| 3,901,657 | 8/1975 | Lightfoot | 422/56 |
| 3,975,162 | 8/1976 | Renn | 422/56 X |
| 3,990,849 | 11/1976 | Lee et al. | 23/230 B |

FOREIGN PATENT DOCUMENTS

| | | | |
|---|---|---|---|
| 2152099 | 5/1973 | Fed. Rep. of Germany | 422/56 |
| 2416047 | 10/1975 | Fed. Rep. of Germany | 422/56 |

Primary Examiner—Arnold Turk
Attorney, Agent, or Firm—S. P. Tedesco

[57] ABSTRACT

There is disclosed a method and apparatus for obtaining a precise aliquot of a sample by diffusing the sample into a gel mass for a controlled period of time. The sample may comprise a liquid containing an unknown quantity of a diffusible, to-be-assayed, component or components. The method may further include reacting a component of the sample with an assay-reagent present in excess quantity above that needed for reaction, the reagent being disposed in the gel mass. The sample is placed in contact with a preselected surface area of the gel mass. The component of the sample is allowed to diffuse into the gel mass for a controlled period of time. Thereafter, the remainder of the sample containing the component is removed, and further diffusion of the component through the gel mass may proceed for a controlled period of time. This provides both a further dilution of the component and permits continuous reaction of the component with a reagent distributed throughout the gel mass. It is possible to measure the degree of reaction between the diffused component and the reagent in the gel mass. Alternatively, the method may involve obtaining an aliquot of a sample containing an unknown quantity of diffusible, to-be-assayed component as above, but without requiring further dilution via diffusion. Also, there may be no need for any assay-reagent and a property of the to-be-assayed component such as color, fluorescence, etc. may be measured directly in the gel mass. In another embodiment, the invention may be practiced so as to obtain a precise aliquot of a sample or of a reagent by diffusing them into a gel mass for a controlled period of time.

18 Claims, 15 Drawing Figures

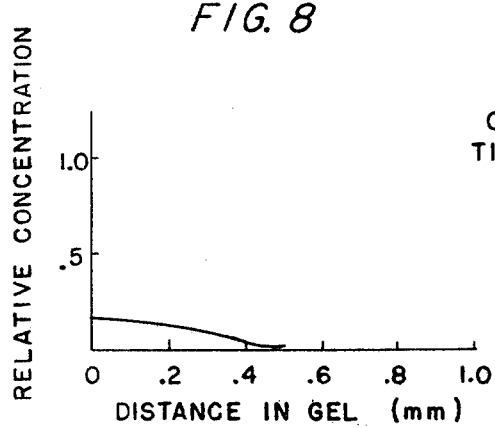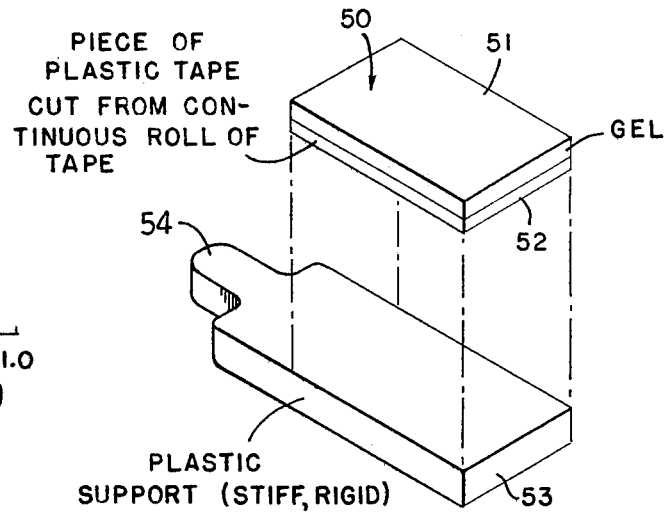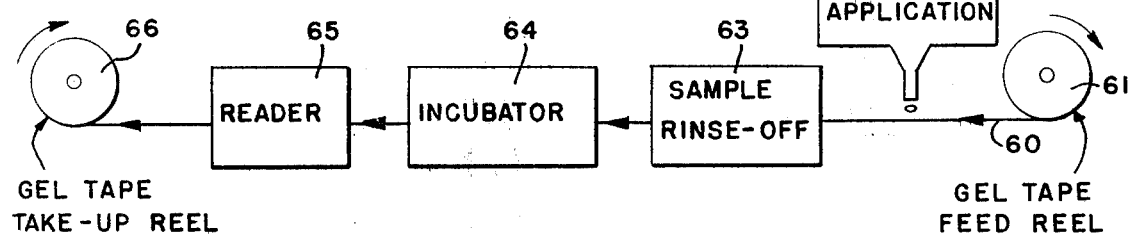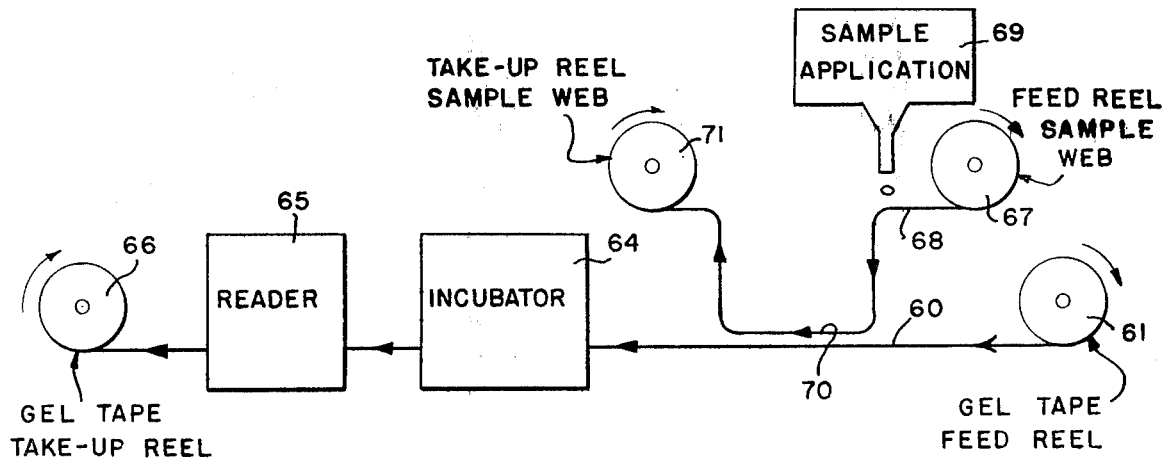

FIG. 12.
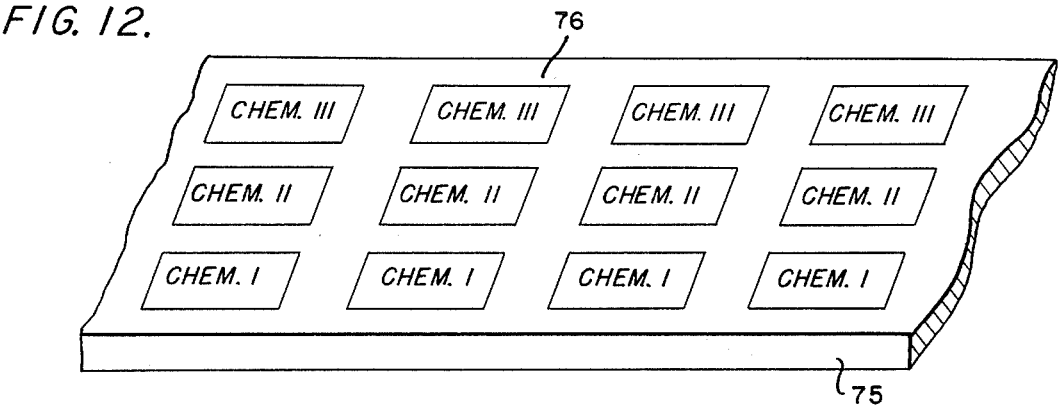
FIG. 13.
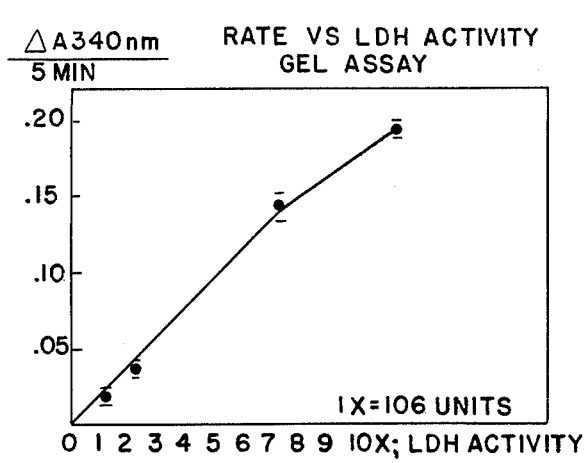
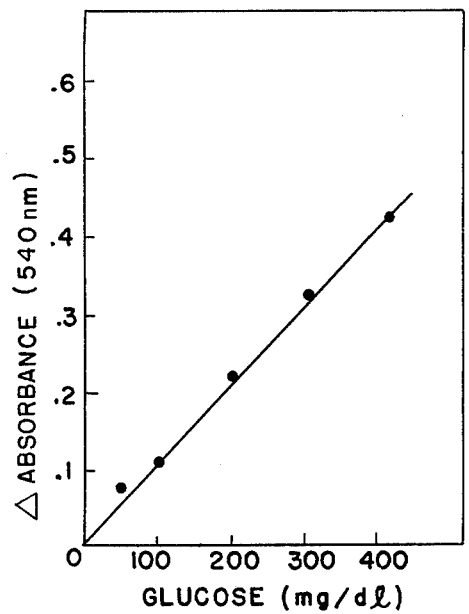
FIG. 15.
FIG. 14.
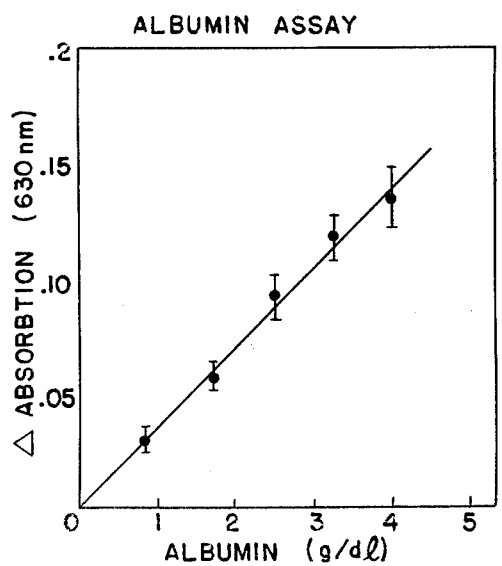

METHOD AND APPARATUS FOR OBTAINING AN ALIQUOT OF A LIQUID IN A GEL MEDIUM

BACKGROUND OF THE INVENTION

It is known that in most liquid-based chemical assays, a sample to be tested must be metered out (a precise aliquot must be delivered) by appropriate means. Additionally, it has been found necessary to meter out diluent for mixing with the sample to achieve an appropriately diluted sample. The step of dilution is usually carried out prior to mixing the sample with the reagent. The reagent must also be metered in an appropriate manner suitable to be employed in a given reaction. The precision of the method of obtaining an aliquot sets the limit of precision of any subsequent analytical measurement. The obtaining of precise aliquot and its dilution are also necessary in order to provide for excess reagent with respect to the sample, and to reduce the effects of interferants.

Both the preparation of the necessary materials and all these steps are time-consuming and inconvenient. The invention seeks a simplified and improved way of obtaining aliquots and dilutions of the to-be-assayed material.

PRIOR ART

Chemical analysis of liquids such as aqueous solutions, foodstuffs like milk, and biological liquids is often desirable or necessary. Various elements to facilitate liquid analyses are known. Such elements have often included an assay-reagent for a substance under analysis (analyte). The reagent, upon reacting with the analyte, effects formation of a colored material or another detectable change. The analyzing elements include, for example, pH test strips and similar indicators wherein a paper or other highly absorbent carrier is impregnated with a material, chemically reactive with said analyte. The material in these test strips responds to contact with liquid containing hydrogen ion or other analytes, and either generates color or changes color. Depending on the selection of the responsive material, the change is usually assessed qualitatively or, at best semi-quantitatively.

In certain fields, it is often required that analytical techniques yield rapid, quantitative results. Much recent development work has attempted to provide elements useful in diagnostic chemical analysis, where testing of biological liquids including body fluids such as blood, serum, urine and the like, must produce highly quantitative results in rapid, convenient fashion.

Analytical techniques applied to chemical solutions have enjoyed broad acceptance in the clinical laboratory environment, particularly in automated analysis. Such techniques, however, require analyzer equipment having intricate solution-handling and transport capabilities. Analytical equipment of the "wet chemistry" variety, illustrated for example in U.S. Pat. No. 2,797,149, is often expensive and may require skilled personnel.

As an alternative to solution chemistry, various multi-layer integral elements for "dry" chemical analysis have been proposed. The term "integral", as used herein to describe analytical elements, refers to elements containing two or more discrete layers. Under conditions of use, these layers are superposed in substantially contiguous contact. Although "dry" analysis offers substantial conveniences in storing and handling materials, the "dry" analysis approach has enjoyed only limited success. It has been used primarily for qualitative and semi-quantitative test purposes.

A variety of multi-layered analytical elements is described in U.S. Pat. No. 3,092,465. Such multi-layer elements use an absorbent fibrous carrier impregnated with one or more reagents. These elements typically include a color former, over which is coated a semipermeable membrane. Upon contact with a test liquid, analyte passes through a membrane into the fibrous carrier. This generates a color in an amount related to the concentration of analyte. The membrane prevents passage and absorption of certain interfering components, such as red blood cells, that could impair the color reading.

Analytical elements that rely on absorbent filter papers or other fibrous media to receive and distribute a liquid sample have not been popular in the clinical laboratory. Presumably this has been due to their inability to produce highly accurate, quantitative results. In U.S. Pat. No. 3,050,373, the use of bibulous materials such as filter papers is suggested. It is mentioned that precipitation can occur in impregnating solutions, thereby impairing uniform distribution of reagent with these bibulous carriers. Also, elements using fibrous, bibulous materials are susceptible to the occurrence of a non-uniformity termed "banding". This is exemplified by a test result occurring to a greater extent in one portion of the element, such as at the periphery of the region penetrated by an applied sample. It is apparently the result of extensive and non-uniform migration of sample components or reagent chemicals within the bibulous material. This may be possibly due to chromatographic effects, which result in highly localized concentrations of such chemicals. Gelatin and gelatin-like materials are described in U.S. Pat. Nos. 3,061,523 and 3,104,209, as useful constituents of an impregnating solution. This is due to their apparent ability to restrain the high rate of migration of sample, and consequently, to provide improvements in test result uniformity. However, gelatin and gelatin-like materials in fibrous, reagent containing, bibulous matrixes decrease the rate of sample uptake as compared to more highly absorbent gelatin-free bibulous matrixes. Such decreased absorption can leave surface liquid on the matrix and necessitate washing the matrix to remove the excess prior to making a test determination. As a result, there is an upper limit on the amount of gelatin to be impregnated into a bibulous matrix. Such properties can also be seen in layers consisting solely of gelatin (or similar) materials, as discussed in U.S. Pat. No. 3,526,480.

Integral analytical elements adapted for automated test procedures have also been described in U.S. Pat. Nos. 3,368,872 and 3,526,480. Such descriptions refer to means for avoiding chromatographic effects (often called ringing, targeting, doughnuting or banding) in the element. These effects are avoided by immobilizing the reagent. The use of simple porous members instead of absorbent, reagent containing materials, such as fibrous filter paper, is suggested. However, there is no suggestion in these descriptions of using a means to aliquot (uniformly receive and dilute) a sample component, such as an analyte, by diffusion through reagent impregnated materials for a controlled period of time. Uniform dilution is extremely important in obtaining quantitative test results, whether by densitometric, colorimetric, fluorimetric, or other readout. This is true even in the absence of gross non-uniformities, such as those introduced by chromatographic effects.

Measuring a detectable reaction change within a fibrous element may be difficult. Many popular reagent-matrix-materials such as filter papers are opaque, allowing detection of an analytical result only at the surface of the matrix material. This diminishes the observable magnitude and range of an analytical result, causing difficulties in measuring low concentrations of analyte. It is desirable to have a transparent matrix material so that that material will not itself introduce variations in the measured optical signal.

Until very recently, there has been no suggestion in the art relating to analytical elements, of a layer to receive sample constituents (analytes) in a uniform manner. In fact, as was apparently well recognized, the structural and chemical characteristics of bibulous and other fibrous materials used (such as absorbent cellulosic filter papers, glass fiber papers, wood, etc.) impaired uniform permeation of sample constituents. Additionally, the choice of fibrous materials can frustrate highly accurate optical measurement due to their severe optical non-uniformity.

Improved multi-layered analytical elements are described in French Pat. No. 2,191,734 and U.S. Pat. No. 3,992,158. Such multi-layered elements can receive a liquid sample and spread the sample within a spreading layer to obtain a uniform concentration of analyte. A precise analytical result can be measured by virtue of the analyte uniformity. Elements disclosed in French Pat. No. 2,191,734, include spreading layers and reagent layers that contain a reactive or otherwise interactive material. By virtue of their uniform activity, these layers promote photometrically reproducible changes.

Recent patents of interest are U.S. Pat. Nos. 3,983,005; 4,042,335; 4,069,016; and 4,069,017. In each of these patents there is taught a migration of a component in a liquid to a substrate matrix containing a reagent. None of the aforementioned patents, however, teach the method of obtaining precise aliquots of sample by diffusing samples into a gel mass for a controlled period of time. Neither do they teach further diffusion as a means to both dilute and react the sample with reagent(s) in the gel medium for a controlled period of time. Further diffusion assures that said sample will become uniformly mixed with an excess of reagent for reacting with said sample.

BRIEF DESCRIPTION OF THE INVENTION

The present invention relates to a process and apparatus to obtain precise aliquots of a component of a sample by diffusing the component into a gel mass for a controlled period of time. Further, the invention also contemplates a method and apparatus of obtaining a precise aliquot of reagent(s). This technique for obtaining precise aliquots may further be useful as a means leading to the packaging of precise amounts of reagents, for example.

It is contemplated that a gel system be employed. The gel may be conveniently charged into a recess or well of a small flat plate, which may approximate the size of a microscope slide for instance. The gel may have incorporated therein, reagent(s) for a given chemical test or tests. It is contemplated that the component (analyte) from the sample be impregnated subsequently into the gel by relying on diffusion. The liquid sample is permitted to overlie a prescribed area of a surface of a previously prepared and hardened gel. The precise aliquot is obtained by diffusion of the analyte into the gel for a relatively precise selected period of time. It should be noted that the volume of liquid sample need not be precisely measured. This eliminates the need for accurate metering by the technician. Such accurate metering by a technician is not only the most time consuming and expensive, but also the most error prone operation in manual testing procedures. Reagents utilized, may be incorporated into the gel system by automated equipment at some convenient time before actual need and use (i.e., well before sample application).

In at least one embodiment of the process of the present invention, a liquid sample containing a component to be quantitatively assayed is spread over a gel surface. The gel contains a reagent for a given test. The sample volume is large enough to cover the entire surface of the gel or a preselected portion thereof. After a period of time sufficient to diffuse a precise aliquot of the component through the defined surface area of the gel, the liquid sample is removed as by washing. Due to the relationship between time and distance in the diffusion laws, analytical errors which may result from any errors in measurement of exposure-time of sample to gel surface, are proportional to the square root of time. Such errors are therefore smaller than analytical errors in conventional liquid assay resulting from time errors. As such, the significance of this invention can easily be appreciated.

In another embodiment, the gel may not need to contain any reagent. For example, hemoglobin, bilirubin, or other light absorbing species may be analytically determined by the above technique without need for reaction with reagents before analysis. Such analytes may be quantitatively measured by known photometric techniques.

It should be further noted that the assay system of the present invention will be operative, with either whole blood, serum, plasma, urine or other biological fluids. The sample may be as small as a drop. Furthermore, as the present invention is employed for assay of diffusible or solubilizable constituents in blood, whole blood may be used. Due to the molecular structure of the gel, the blood cells cannot migrate into the gel. Therefore, there is no need to effect a separation of the serum or plasma from the cells prior to analysis.

It is contemplated that sample consituents other than the analyte of interest may also diffuse into the gel from the liquid sample. As this will occur, the assay reagent selected for discernible reaction will be selected with a certain degree of care. Also, selection of appropriate "pore sizes" charge and functional groups in the gel may be used to obtain selectivity towards preferential diffusion of desired constituents. In the case where the assay reagent has been previously incorporated into the gel, the concentration of the reagent in the gel is typically uniform. After the liquid sample has been removed from the surface of the gel, a further diffusion may take place for a preselected exposure time. During this time, the components that have been introduced into a surface zone of the gel, diffuse further throughout the gel. This allows the analyte to be diluted to a concentration which is less than that which would prevent complete reaction with reagent within the gel. Simultaneously with this dilution, the analyte will react with the reagent in the gel. It will be evident, therefore, that precise measuring of analyte (aliquots) is obtained by the inventive method and apparatus by timing without the previously known inefficiency and inconvenience of metering of volumes.

OBJECTS

It is an object of this invention to provide an improved method and apparatus for obtaining precise aliquots of samples and/or reagents;

It is another object of the invention to provide an improved method and apparatus for analyzing a sample containing an analyte;

It is still a further object of the invention to provide a method and apparatus for obtaining an aliquot of an analyte of a sample by means of diffusing said analyte into a gel medium;

It is yet another object of this invention to provide a method and apparatus analyzing whole blood without requiring prior separation of its constituents;

It is still another object of the invention to provide a method and apparatus for analyzing whole blood without need for a conventional washing step after diffusion of the blood sample into a gel medium.

These and other objects of this invention will become more apparent and will be better understood with respect to the following detailed description taken in conjunction with the accompanying drawings, in which:

FIG. 8 is a graph showing analyte penetration into the gel after incubation.

FIG. 9 is another embodiment showing a perspective view of a dip stick configuration of the inventive apparatus.

FIG. 10 is another embodiment showing an automated system in a diagrammatic manner.

FIG. 11 is yet another embodiment showing an automated system also in a diagrammatic manner.

FIG. 12 is a perspective view of an example of a continuous tape construction which is another embodiment of the present invention.

FIG. 13 is a graph showing LDH assay.

FIG. 14 is a graph showing glucose assay.

FIG. 15 is a graph showing albumin assay.

DETAILED DESCRIPTION OF THE EMBODIMENTS OF THE INVENTION

Figure 1:
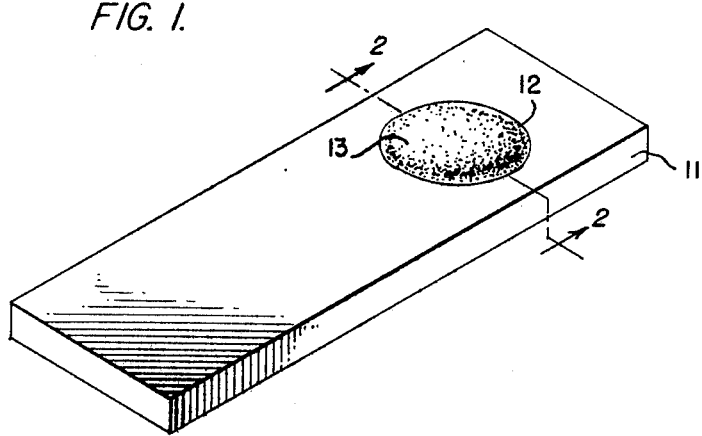
FIG. 1 is a perspective view of one embodiment of the present invention.
Figure 2:
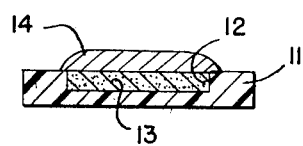
FIG. 2 is a cross-sectional view of FIG. 1 taken along line 2—2 with a drop of sample in place.

Attention is now directed to the drawings for a consideration of various structural embodiments of the invention. It will be noted that in FIG. 1 a flat rectangularly shaped support 11 is provided. The support possesses a well 12 provided in a conventional manner which is filled with a gel 13 containing a reagent. The support 11 may be constructed of plastic or glass. While dimensional characteristics are not extremely important, it is contemplated that the well 12 will be of from 0.1 to 2 mm in thickness and of from 5 to 20 mm in diameter. The embodiment disclosed in FIGS. 1 and 2, employs a well 12 of 1 mm in depth and 8 mm in diameter. The well is generally centered on the support 11 at a location wherein the gel will intersect the light beam of a suitable photometer or spectrophotometer. The gel should preferably fill the well to the surface whereby good contact is made with the supply of the liquid sample. For instance, when a drop of sample 14 is utilized, the drop must overlap the annular portion of the support surrounding the well. The necessity of filling the well to its fullest extent with the gel is even more important when the application of the sample is by way of supplemental carrier. For example, a liquid sample may be incorporated in a capillary web. Such a web is then brought into touching confrontation with the surface of the gel. A portion of the sample, such as an analyte, diffuses into the gel directly from the sample loaded capillary web. After a preselected period of time, the web may be removed from the surface of the gel. The analyte that has penetrated into a portion of the gel is then permitted to diffuse still further during an incubation period. At the end of the incubation period, the gel is analyzed by conventional means.

Figure 3:
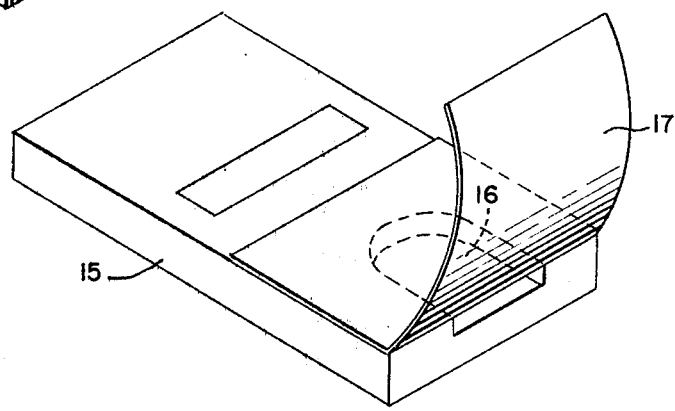
FIG. 3 is a perspective view of another embodiment of the present invention with a flexible cover over a portion of the to-be-filled cavity.
Figure 4:
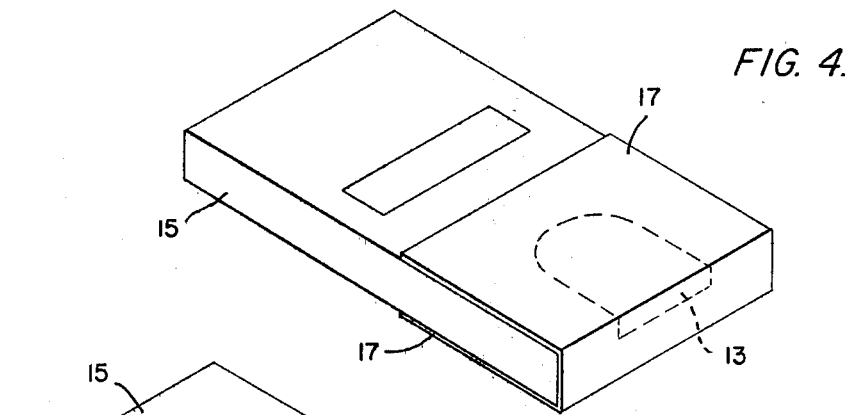
FIG. 4 is a perspective view as in FIG. 3 with a transparent tape closing off the entire cavity having been filled with reagent containing gel.
Figure 5:
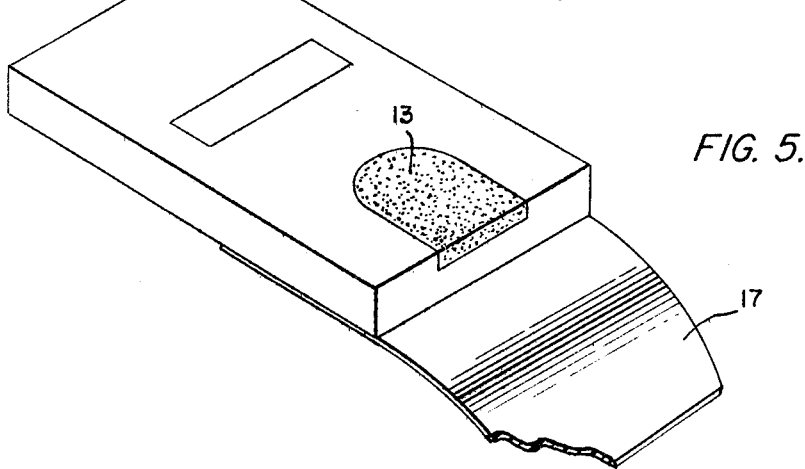
FIG. 5 is a perspective view as in FIGS. 3 and 4 with the transparent tape in the process of being removed.

Attention is now directed to FIGS. 3, 4 and 5. It is here taught that a support 15 has a U-shaped cavity 16 at one surface of the support 15. The broad end of the cavity 16 is open at the end of the support. The arrangement of this embodiment lends itself to large-scale fabrication. This is accomplished by sealing the major open surface of a plurality of like supports with pressure sensitive adhesive tape 17, but with the end portion of the cavity in an open condition, through which the gel 13 may be loaded into the cavity. The gel is permitted to harden, thereafter the remaining loose portion of the adhesive tape 17 is wrapped around the end of the support to seal the remaining portion of the cavity 16. In this embodiment, the device may be used as a dip stick for immersion in the sample for a predetermined time. The tape 17 is removed prior to use. The dip stick is then immersed in the liquid sample for a predetermined period of time which is sufficiently short to permit diffusion of sample analyte into only a relatively shallow surface layer of the gel medium. The gel will usually contain a reagent which has been preloaded therein. The analyte will react with the reagent as it diffuses. The proportions of the reactants are well chosen to insure a complete reaction, i.e., more reagent than analyte. The reaction may be conventionally monitored.

Figure 6:
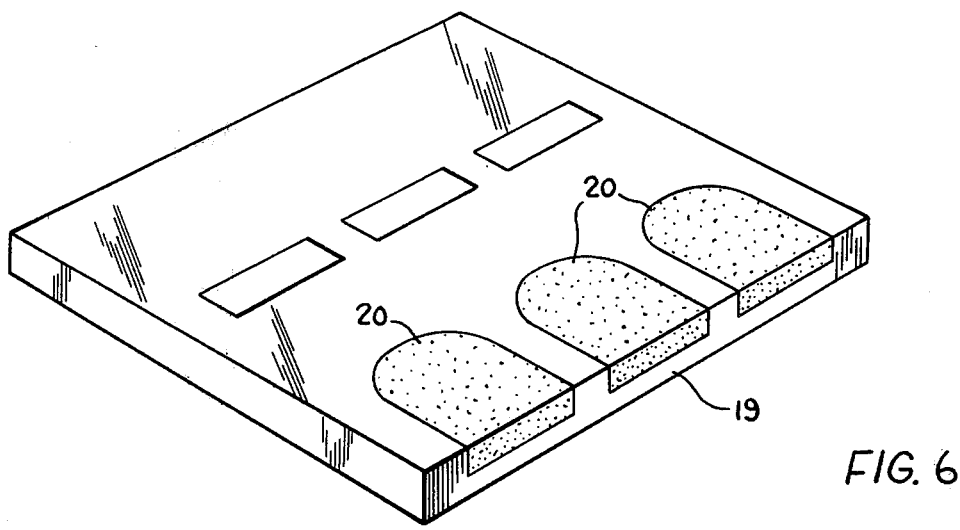
FIG. 6 is a perspective view of yet another embodiment of the present invention.

FIG. 6 is similar to the embodiments shown in the aforementioned embodiment of FIGS. 3, 4 and 5. A plurality of cavities 20 are disclosed however, so that a plurality of test or assays may be performed on a single support 19.

In the foregoing, the assembly has been a substrate having a well therein, or at least some sort of depression. Within the purview of the instant matter, it is indeed contemplated that a dip stick also be constructed from a specially prepared roll of tape. Accordingly, attention is directed to FIG. 9 for such an arrangement. Initially, an elongated transparent tape is given a coating of a gel on at least one surface. The gel is permitted to set up or harden thereon, although a certain degree of flexibility may be desirable for handling purposes. The gel is as before, i.e., charged with a reagent for use in producing a reaction with an analyte in the sample.

The resultant tape is cut into suitable composite lengths 50 as shown in exploded FIG. 9. The gel 51 is facing upwardly, while the tape substrate 52 is underneath. The substrate 52 has an amount of an adhesive coated on its underside. The composite is secured to a fairly rigid plastic support 53 which may be relatively longer than the length 50. The extended portion may comprise a handle 54, by means of which the dip stick may be inserted in a quantity of liquid sample as heretofore mentioned.

It is further contemplated that the tape shown in FIG. 9, may be used in a form whereby portions are not cut, but the entire roll is used in an automated system. Accordingly, attention is directed to FIG. 10. Reading from right to left, note that a gel tape 60 is unwound from a feed reel 61 and travels horizontally along a path delineated by arrows. The tape 60 passes a sample actuator station 62, whereat discrete liquid samples are dropped. The path and traversing speed of the tape is such, that sufficient diffusion will take place in the surface area of the gel for a short depth. At station 63, the remaining liquid sample is briefly rinsed away by suitable means well known in the art. At the next station 64, the tape is incubated to permit further diffusion in the manner as heretofore suggested. Thereafter, the tape 60 is delivered to a reader station 65, at which point the reactant areas are optically read in a conventional manner. The tape may then be rewound by a take-up reel 66.

In the foregoing embodiment, the tape substrate may be any one of several well known transparent plastic materials, such as polyethylene terphthalate (mylar), polyethylene, polypropylene, methyl-methacrylate (lucite), etc.

Attention is now directed to FIG. 11 for a review of still another automated system shown in a schematic manner. Again, a gel tape 60 is positioned on a reel 61. In this embodiment, the sample drop is not applied directly to gel tape 60. Rather, a secondary supply reel 67 is employed which carries an aqueous permeable web 68. The web 68 may be comprised of cellulose, nylon, or a material usefully employed as a dialysis type membrane. The web 68 is discharged from reel 67 along a path that traverses a sample application station 69. The sample application station 69, delivers a sample drop to web 68. The sample drop penetrates the web 68 by diffusion or capillary action, thus allowing the sample to wet the gel tape 60 through the underside of web 68 as it comes into touching contact at position 70. A sufficient period of time is needed to cause diffusion of the sample from tape 68 into the gel tape 60. After the web 68 and the tape 60 part, the web 68 is wound on take-up reel 71. The tape 60 in the meantime continues travelling along its path (delineated by arrows) to an incubator 64. Thereafter, the tape is advanced to the measuring station 65 for analysis purposes. Finally, the tape 60 is wound upon the take-up reel 66.

It will be appreciated that the present invention lends itself to the concept of performing various clinical chemical assays. In the foregoing systems of FIGS. 10 and 11, the discussion pertained to the same assay being performed on a plurality of samples. Attention is now directed to FIG. 12 for a review of an arrangement for undertaking not only an assay on a plurality of samples, but also undertaking suitable steps to achieve a plurality, e.g., three different clinical chemical assays. It will be noted that this can be accomplished by employing an elongated tape 75 of e.g., mylar, or cellophane. The embodiment shown in FIG. 12 is in fragmentary form.

A series of "chips" 76 are prepared as in connection with dip stick arrangement of FIG. 9, wherein a gel tape is provided as "chips" 76. The "chips" 76 are adhesively positioned in spaced-apart relationship on tape 75. The first row of "chips" 76 may be all devoted, for example, to an albumin assay. The second row of "chips" 76 may all be used for a glucose assay, for instance. Finally, the third row may be for a lactate dehydrogenase (LDH) assay.

Also, it is evident that a series of "chips" 76 can be provided on tape 60 of FIGS. 10 and 11, whereby different chemical assays can be effected with respect to each successive sample applied to tape 60. In such event, the measuring station 65 is adapted to analyze the reaction results obtained in corresponding "chips" in correlated fashion with respect to each sample.

In the foregoing system, a series of discrete "chips" 76 are shown. It is also contemplated that the chips may be non-discontinuous so that parallel elongated strips may be employed, i.e., one for each of the selected assay as desired.

Linearity in a chemical assay system is an important criterion of reliable performance. Linearity implies a first order kinetic reaction so that concentration of test substance may be easily assayed. It is well known that in order to obtain linearity, it is necessary to have excess reagent. This is accomplished here by carrying out the assay in a two-step process.

Figure 7:
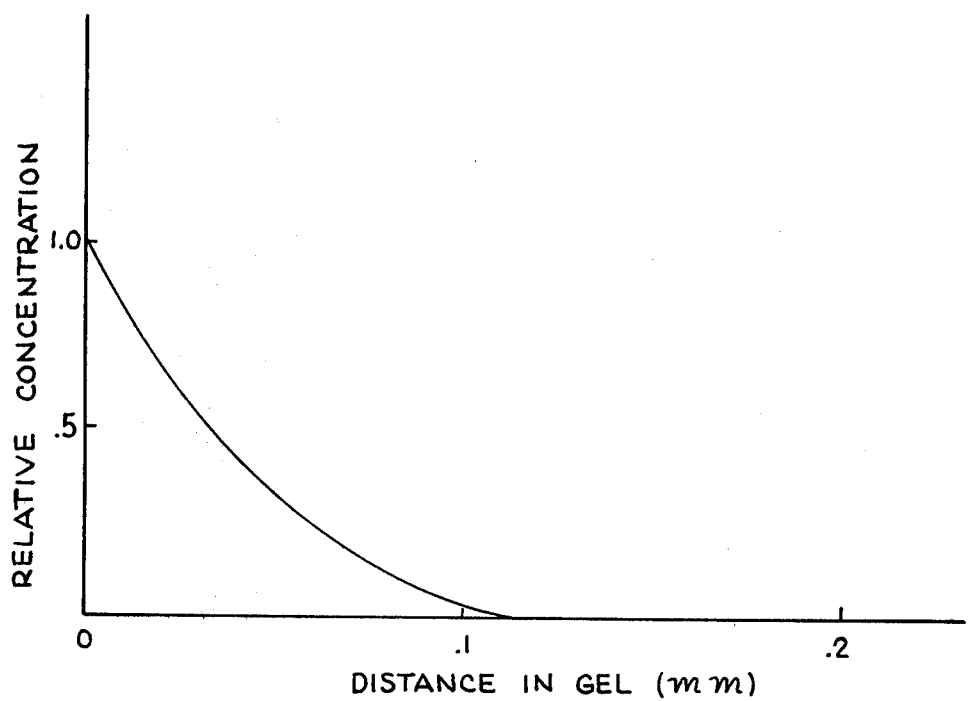
FIG. 7 is a graph showing initial gel penetration by an analyte of a sample.

The operation of the aforementioned sytems will be described in the following discussion. Contact is made between the surface of the gel and the sample for a brief period of time, i.e., of the order of 10 to 60 seconds. The sample is then removed. It has been discovered that this will allow diffusion of the sample analyte into the surface region of the gel. It should prove evident that conditions may easily be selected, whereby the depth of penetration of the analyte molecules will be small relative to the thickness of the gel. This procedure will create a "reservoir" of analyte near the outwardly facing portion of the gel. For example, FIG. 7 depicts a graph showing a diffusion profile for albumin on 1% agarose for 20 seconds (free diffusion in a gel media). Note that in the 20 seconds the average distance of diffusion of the albumin is approximately 0.05 mm into the gel. In FIG. 8, the graph shows the distance travelled by the albumin after 5 minutes of incubation following 20 seconds exposure to the sample.

To be most effective, a further diffusion of the analyte into the gel is required after removal of the sample liquid from contact with the gel surface. This will permit redistribution of the sample throughout the gel. It is submitted that the subsequent diffusion is equivalent to performing the mixing of a known dilution of the sample substance in comparable solution chemistries. The sample will now be distributed throughout the gel with equal concentration at all points and lower than in the original sample being tested. It will be appreciated that by means of this arrangement of a two step diffusion process, the usual prior art dilution process has been replaced. This method is also useful in diluting interferants in the sample, thereby lessening their influence on the analysis. Furthermore, because of the sample dilution, smaller concentrations of reagents are required to completely react with the sample. Such salutary conditions are advantageous for the establishment of first order reaction kinetics and calibration curves that are linear with analyte concentration. However, as previously stated, the time dependency of the reaction is not linear due to the fact that the distance of diffusion is a square root function of time. Thus, errors in measuring the time during which the gel is exposed to a liquid sample produces smaller analytical errors that are proportional only to the square root of time.

As used herein, the term gel relates to a matrix in which the interactive material is distributed, i.e., dissolved or dispersed. The choice of a matrix material is, of course, variable and dependent on intended use. Desirable matrix materials for gel media can include hydrophilic materials including both naturally occurring substances like gelatin, gelatin derivatives, hydrophilic cellulose derivatives, polysaccharides such as dextran, gum arabic, agarose and the like, and also synthetic substances such as water-soluble polyvinyl compounds like poly(vinyl alcohol) and poly(vinyl pyrrolidone), acrylamide polymers, etc.

It is contemplated that any analytical procedure can be adapted to the herein disclosed invention. While the apparatuses and methods herein disclosed are particularly suitable for routine blood chemistry such as glucose, blood urea, nitrogen, uric acid, albumin, creatinine, bilirubin, phosphate, total protein, amylase, calcium, etc., numerous other analytical tests which are run periodically can be automatically performed in accordance with the precepts of the invention.

Having discussed the various embodiments and operation of the systems that are useful in carrying out the precepts of the invention, it is incumbent to now complete this disclosure by including a number of specific examples relative to undertaking assays.

EXAMPLE I

In a typical system for the assay of the enzyme lactate dehydrogenase (LDH), a 1 mm thick gel is prepared from an aqueous solution containing 6.0 mM nicotine adenine dinucleotide, 100 mM lithium lactate, 1% by weight agarose and AMP buffered at 0.72 M to a pH 9.0. The exposure time for the LDH containing solution was for a duration of one minute, after which time it was removed. The rate of change of absorbance at 340 nm followed over the next 3 to 5 minutes. It was noted that such a system gives linear absorbance versus time curves for the first five minutes of incubation with LDH concentrations up to 700 units/ml, as shown in FIG. 13.

EXAMPLE II

A second typical system includes the assay of glucose. A 1 mm thick gel was prepared containing 4-chloro-1-napthol (0.006%) glucose oxidase (120,000 units/liter), peroxidase (170,000 units/liter), phosphate buffered saline (0.01 M, pH 7.0) and agarose (1%). Various test solutions containing up to 400 mg/dl were tested by employing sample exposure times of 15 seconds. Thereafter, 10 minutes of incubation time was employed. Absorbance at 540 nm wavelength was then measured. Such a system gives linear calibration curves for glucose concentrations up to 400 mg/dl, as illustrated in FIG. 14.

EXAMPLE III

A typical system for assay of albumin was Bromocresol Green (32 mg/100 ml) in a pH 4.2 succinate buffer with 0.5% Brij 35 in 1% agarose. Exposure time to albumin may be 20 seconds, and total incubation time thereafter may be 10 minutes. Such a system gives linear results from 0 to 5% albumin, with a precision of ±2-3% as can be discerned from FIG. 15. The reaction is complete after 10 minutes, with no change in color occuring thereafter. It should be noted that albumin is a large molecule, but the gel porosity easily can be made large enough to permit its facile entry.

The invention has been described in detail with particular reference to certain preferred embodiments thereof, but it will be understood that variations and modifications can be effected within the spirit and scope of the invention.

Having thus described the invention, what is sought to be protected by Letters Patent is presented in the following appended claims.

What is claimed is:
1. A method of analyzing a sample comprising the steps of:
    (a) contacting a surface of a gel mass containing a given quantity of reagent with a sample containing an analyte;
    (b) diffusing at least a portion of said sample into said gel mass for a first period of time to obtain a precise aliquot of analyte within said gel mass which is less than said given quantity of reagent;
    (c) further diffusing said aliquot through said gel mass for a second period of time to obtain a desired dilution of said analyte and achieve a complete reaction with said reagent;
    (d) separating the non-diffused portion of sample from said surface of the gel mass after said first period of time; and
    (e) measuring said reaction.
2. The method of claim 1, wherein said analyte is reacted with more than one reagent.
3. The method of claim 1, wherein said separating step (d) is achieved by washing said non-diffused portion of sample from said surface of the gel mass.
4. The method of claim 1, wherein said sample is whole blood.
5. The method of claim 1, wherein said gel mass is a hydrocolloid.
6. The method of claim 1, wherein said measuring step (d) includes photometrically measuring said analyte.
7. The method of claim 1, wherein said analyte comprises at least one component of a biological sample.
8. The method of claim 1, wherein said gel mass is transparent and wherein said measuring step (e) includes measuring said reaction through said gel mass.
9. The method of claim 1, wherein the contacting step (a) includes dispensing said sample to overlap a prescribed surface area of said gel mass.
10. The method of claim 1, wherein said analyte comprises a catalyst, such as an enzyme, and the measuring step (d) comprises measuring the rate of reaction.
11. The method of claim 1, wherein the diffusing step (b) comprises the steps of:
    (f) supporting said sample on a carrier; and
    (g) contacting said supported sample to said gel mass during said first period of time.
12. The method of claim 11, wherein said carrier is a porous medium, and the supporting step (f) includes impregnating such medium with said sample.
13. A method of obtaining a precise aliquot of a substance in distribution throughout a gel mass, comprising the steps of:
    (a) contacting a prescribed surface area of a gel mass with an excess quantity of said substance;

(b) diffusing said substance into said gel mass for a controlled period of time to introduce a precise aliquot of said substance into said gel mass;

(c) removing non-diffused substances from said surface area after said period of time; and (d) further diffusing said aliquot within said gel mass to distribute said substance throughout said gel mass.

14. The method of claim 13, comprising the further step of supporting the substance on a carrier and wherein the contacting step (a) includes contacting said carrier and said gel mass and the removing step (c) includes separating said carrier and said gel mass.

15. The method of claim 13, wherein said removing step (c) is achieved by washing said substance from said surface of the gel mass.

16. The method of claim 13, wherein said gel mass is a hydrocolloid.

17. The method of claim 13, wherein the contacting step (a) includes dispensing said substance to overlap said prescribed surface area.

18. The method of claim 17, comprising the further step of defining said prescribed surface area in planar fashion.

* * * * *